(12) United States Patent
Stuffel

(10) Patent No.: US 8,721,700 B2
(45) Date of Patent: May 13, 2014

(54) THERAPEUTIC HEATED POCKET

(76) Inventor: Gene Stuffel, Wendell, NC (US)

( * ) Notice: Subject to any disclaimer, the term of this patent is extended or adjusted under 35 U.S.C. 154(b) by 384 days.

(21) Appl. No.: 13/083,546

(22) Filed: Apr. 9, 2011

(65) Prior Publication Data

US 2012/0046719 A1 Feb. 23, 2012

Related U.S. Application Data

(60) Provisional application No. 61/375,772, filed on Aug. 20, 2010.

(51) Int. Cl.
*A61F 7/08* (2006.01)

(52) U.S. Cl.
USPC ........... 607/111; 607/108; 607/109; 607/110; 607/112; 219/211

(58) Field of Classification Search
USPC .......................................... 607/111; 219/211
See application file for complete search history.

(56) References Cited

U.S. PATENT DOCUMENTS

| | | | | |
|---|---|---|---|---|
| 1,358,509 A * | 11/1920 | Birkenfeld | ...................... | 219/211 |
| 2,298,298 A * | 10/1942 | Joy et al. | ...................... | 219/211 |
| 2,579,383 A * | 12/1951 | Goudsmit | ...................... | 219/211 |
| 2,769,892 A * | 11/1956 | Collins | ...................... | 607/111 |
| 3,710,075 A * | 1/1973 | Jablonowski | ...................... | 607/108 |
| 3,748,436 A * | 7/1973 | Cossaboom | ...................... | 219/211 |
| 3,869,594 A * | 3/1975 | Shively | ...................... | 219/211 |
| 3,874,000 A * | 4/1975 | Altman | ...................... | 2/158 |
| 4,021,640 A * | 5/1977 | Gross et al. | ...................... | 219/211 |
| 4,042,803 A * | 8/1977 | Bickford | ...................... | 219/211 |
| 4,107,509 A * | 8/1978 | Scher et al. | ...................... | 607/108 |
| 4,221,954 A * | 9/1980 | Cohen | ...................... | 219/212 |
| 4,404,460 A * | 9/1983 | Kerr | ...................... | 219/211 |
| 4,461,299 A * | 7/1984 | Guibert | ...................... | 607/96 |
| 4,736,088 A * | 4/1988 | Bart | ...................... | 219/211 |
| 5,032,705 A * | 7/1991 | Batcheller et al. | ...................... | 219/211 |
| 5,405,370 A * | 4/1995 | Irani | ...................... | 607/104 |
| 5,484,448 A * | 1/1996 | Steele et al. | ...................... | 607/108 |
| 5,986,243 A * | 11/1999 | Campf | ...................... | 219/529 |
| 6,094,599 A * | 7/2000 | Bingham et al. | ...................... | 607/149 |
| 6,123,717 A * | 9/2000 | Davis et al. | ...................... | 607/109 |
| 6,468,295 B2 * | 10/2002 | Augustine et al. | ...................... | 607/96 |
| 6,714,821 B1 * | 3/2004 | Duda et al. | ...................... | 607/98 |
| 6,716,235 B2 * | 4/2004 | Augustine et al. | ...................... | 607/96 |
| 6,727,469 B1 * | 4/2004 | Parker et al. | ...................... | 219/211 |
| 6,860,896 B2 * | 3/2005 | Leber et al. | ...................... | 607/1 |
| 6,902,574 B2 * | 6/2005 | Graham et al. | ...................... | 607/111 |
| 7,693,580 B2 * | 4/2010 | Docherty et al. | ...................... | 607/98 |
| 7,783,361 B2 * | 8/2010 | Docherty et al. | ...................... | 607/100 |
| 8,084,722 B2 * | 12/2011 | Haas et al. | ...................... | 219/543 |
| 8,133,264 B1 * | 3/2012 | Lafontaine | ...................... | 607/112 |
| 8,170,685 B2 * | 5/2012 | Docherty et al. | ...................... | 607/100 |
| 8,258,443 B2 * | 9/2012 | Caterina et al. | ...................... | 219/530 |
| 2004/0044384 A1 * | 3/2004 | Leber et al. | ...................... | 607/88 |

(Continued)

*Primary Examiner* — Linda Dvorak
*Assistant Examiner* — Kaitlyn Smith
(74) *Attorney, Agent, or Firm* — Mind Law Firm, P.C.; Justin G. Sanders; Jeromye V. Sartain

(57) ABSTRACT

A therapeutic heated pocket and method of use in accordance with the present disclosure generally comprises an outer covering, edge trim, baby-dry material, insulation material, headliner material, heating coil, heating element, power cord and power adjustment controller. The pocket allows an arthritis sufferer to quickly and evenly warm an affected area in order to increase blood flow to the area. This has been shown to increase mobility and decrease pain for several hours after use.

15 Claims, 3 Drawing Sheets

(56) References Cited

U.S. PATENT DOCUMENTS

| | | | |
|---|---|---|---|
| 2004/0147990 A1* | 7/2004 | Graham et al. | 607/111 |
| 2006/0052849 A1* | 3/2006 | Docherty et al. | 607/100 |
| 2006/0052855 A1* | 3/2006 | Docherty et al. | 607/108 |
| 2008/0009926 A1* | 1/2008 | Russak et al. | 607/109 |
| 2008/0083720 A1* | 4/2008 | Gentile et al. | 219/211 |
| 2008/0083721 A1* | 4/2008 | Kaiserman et al. | 219/211 |
| 2008/0083740 A1* | 4/2008 | Kaiserman et al. | 219/520 |
| 2008/0197126 A1* | 8/2008 | Bourke et al. | 219/634 |
| 2008/0234789 A1* | 9/2008 | Freeland et al. | 607/108 |
| 2008/0262393 A1* | 10/2008 | Docherty et al. | 601/15 |
| 2009/0054959 A1* | 2/2009 | Felker | 607/111 |
| 2011/0306943 A1* | 12/2011 | Dunbar et al. | 604/291 |
| 2011/0307040 A1* | 12/2011 | Peterson | 607/108 |
| 2012/0004738 A1* | 1/2012 | Westrate | 623/36 |
| 2012/0191164 A1* | 7/2012 | Gander et al. | 607/96 |

* cited by examiner

THERAPEUTIC HEATED POCKET

CROSS REFERENCE TO RELATED APPLICATIONS

This application claims the benefit of 35 U.S.C. §119 and the filing date of provisional application 61/375,772, filed Aug. 20, 2010.

FIELD OF INVENTION

The present invention relates to the field of medical devices. More specifically, the invention relates to medical devices and a therapeutic device for the treatment of arthritis.

BACKGROUND OF THE INVENTION

Arthritis sufferers often experience pain and swelling in various joints of the body to the extent that they are not able to fully utilize their own body. Various methods of treating the problem, such as taking pain killers, blood thinners and inflammation reducers like Aspirin are not always the healthiest way to solve the problem.

In efforts to alleviate these problems, various articles of clothing and coverings which actively supply heat to the body have been previously devised. Some of these devices involve mixing chemical solutions within internal chambers. Others involve using gel materials that can be heating before application. One attempt to solve the problem, as disclosed in U.S. Pat. No. 4,173,218, employs the use of splinted fingers within a glove to minimize the impact from painful jolts. Like the previous inventions, this device also uses a fluid filled layer.

Other patents, have tried to use gloves with fabrics made of metal. These often do not contain the correct amount of insulation to protect a person wearing the gloves from electric shock and can disperse heat unevenly. These devices also have obvious limitations due to a battery generated power source. For example, U.S. Pat. No. 4,764,665 discloses a wired material that must wrap around the fingers and uses a busbar. The instant disclosure does not rely on these restrictions nor require such complicated wiring. Instead, it uses the correct amount of layering so that any anatomical structure will receive a safe and even amount of warmth for the desired amount of time due to its insulative properties.

The present invention employs a combination of material not used in the prior art to create a therapeutic pocket. After just a brief period of use, this therapeutic pocket can provide an arthritis sufferer with hours of relief.

SUMMARY OF THE INVENTION

A therapeutic heated pocket and method of use in accordance with the present disclosure generally comprises an outer covering, edge trim, baby-dry material, insulation material, headliner material, heating coil, heating element, power cord and power adjustment controller.

DETAILED DESCRIPTION OF THE PREFERRED EMBODIMENT

In the following description of the various embodiments, reference is made to the accompanying drawings, which form a part hereof, and in which is shown by way of illustration, various embodiments in which the invention may be practiced. It is to be understood that other embodiments may still be utilized and structural and functional modifications may be made without departing from the scope and spirit of the present invention.

Figure 1:
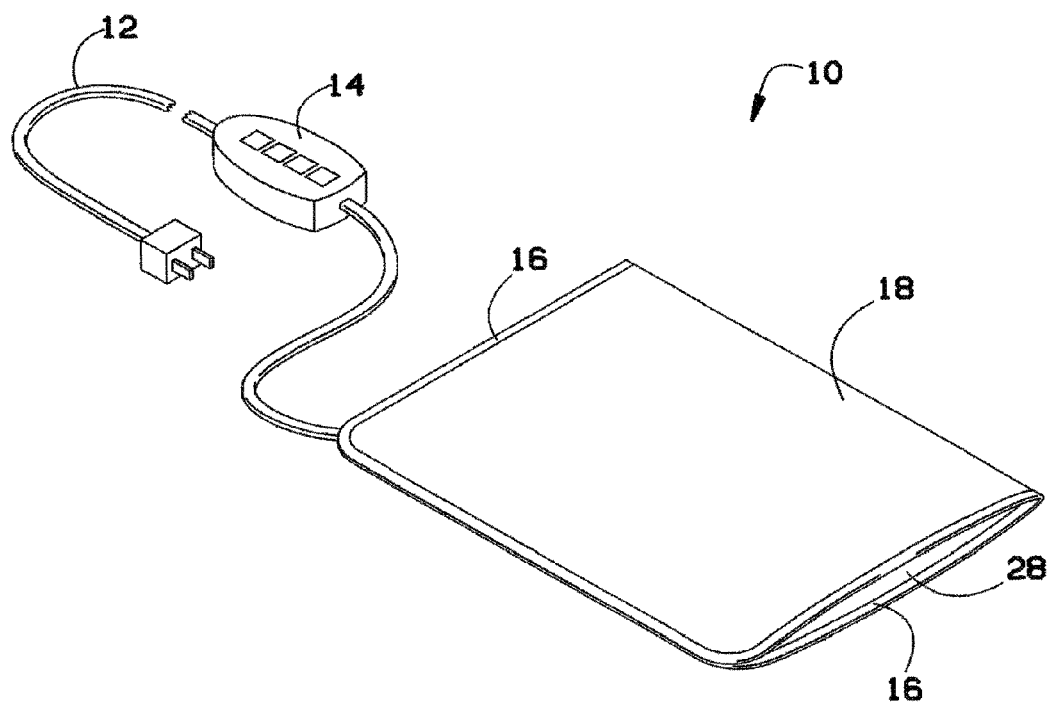
FIG. 1 illustrates a perspective view of the preferred embodiment of the present invention.

Referring to FIG. 1, a perspective view of the preferred embodiment of a therapeutic heated pocket is shown. Amongst other elements, pocket 10 comprises outer cover 18, edge trim 16, baby dry material 28, controller 14 and power cord 12. In operation, heated pocket 10 provides therapeutic (conductive and?) radiated heat to the affected parts of the body that fit within pocket 10, such as the hands, knees, elbows or feet. By increasing circulation and blood flow to an affected area, the device aids in reducing stiffness in joints and associated pain. In the preferred embodiment, outer cover 18 is composed of 65% polyester and 35% cotton. Outer cover 18 folds to completely cover the outer surface of pocket 10 except for an entry area on the right side of pocket 10 as shown. Edge trim 16 forms a continuous loop to seal the edges of outer cover 18. Edge trim 16 may be stitched, glued, or permanently attached to outer cover 18 in any manner known in the art. In one embodiment, can it be unfolded and opened to apply on an area such as a back, neck or shoulder.

Figure 2:
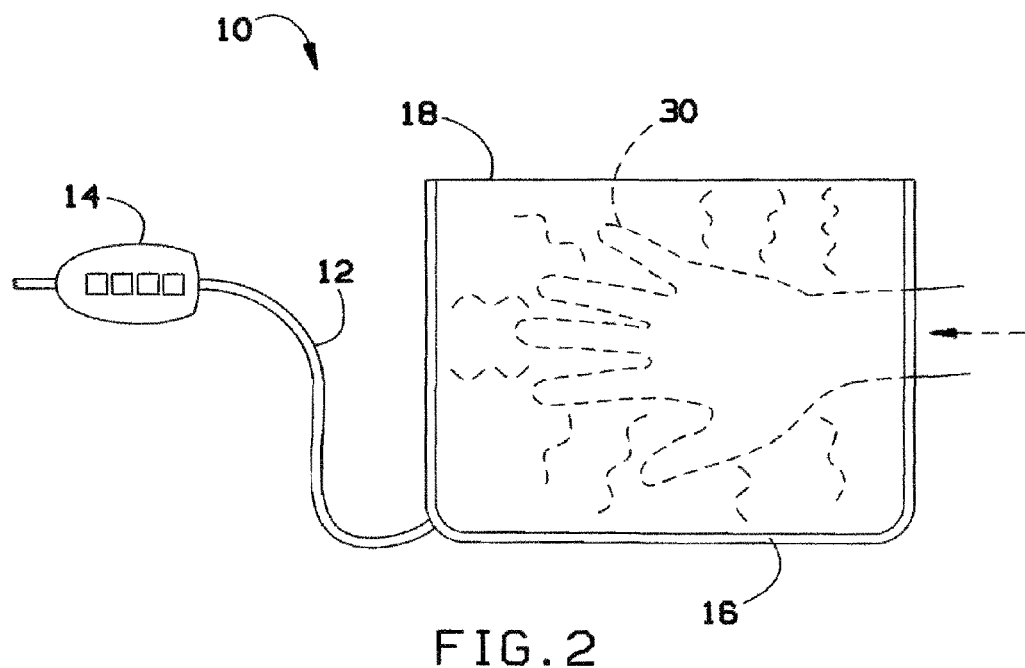
FIG. 2 illustrates a plan view of the preferred embodiment of the present invention while in use.

Now referring to FIG. 2, a plan view of the preferred embodiment of the present invention in use is shown. For exemplary purposes, an arthritic hand 30 is shown being inserted into the entry area of pocket 10. Being completely wrapped with the various layers of pocket 10, including outer cover 18 and sealed with edge trim 16, heat is transferred from the layers of the device to hand 30. In alternate embodiments of the present invention, other anatomical and affected areas of the body can be substituted for hand 30. Additionally, pocket 10 can be used to reduce the symptoms of a variety of diseases that involve swelling and pain, including but not limited to osteoarthritis, rheumatoid arthritis, other rare forms of arthritis, gout, lupus, psoriasis and even for physical therapy after sports injuries such as sprains of the ligaments and tears of the cartilage. Finally, power cord 12 provides an electrical connection between pocket 10 and controller 14. Controller 14 allows the user to adjust the device to emit different amounts of heat and may have up to four different specific heat settings, or in other embodiments have a continuum of heat settings. In alternate embodiments, controller 14 may further comprise a computer that allows for a myriad of operational programs and settings.

Figure 3:
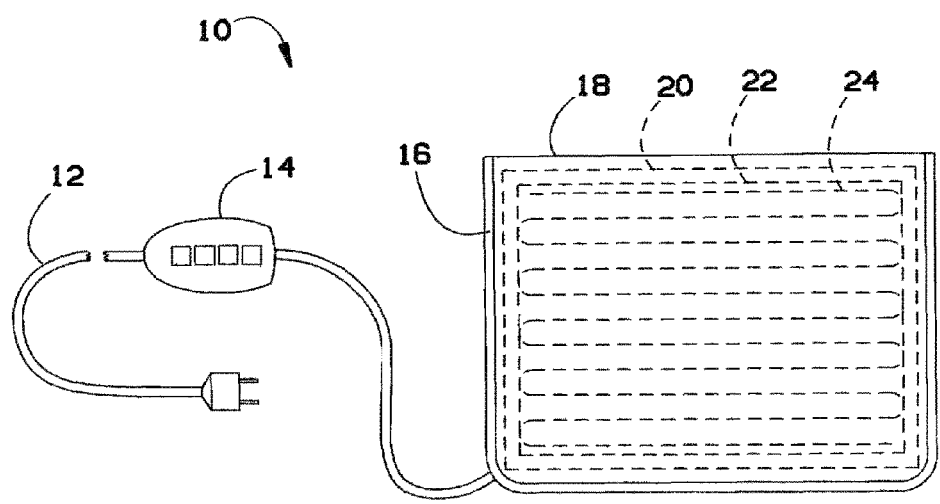
FIG. 3 illustrates an alternate plan view of the preferred embodiment of the present invention.

Now referring to FIG. 3, an alternate plan view of the preferred embodiment of the present invention is shown. Outer surface 18 can be seen encompassing the various internal layers and wiring of pocket 10. These layers will be described in greater detail in FIG. 8. For now, insulation material 20 alone may contain four individual layers. These layers may be composed of various materials, alone or in combination, such as cotton, wool, aluminum foil, polyester and other materials known for their insulative properties, with the aluminum as the outer layer. Thus, in at least one embodiment, the insulation material 20 is comprised of at least three materials of the group consisting of wool, polyester, cotton and aluminum. Insulation 20, with minimum heat retention of 81 %, keeps a majority of generated heat within the pocket and focused on the affected area. The fabric side of insulation 20 may be glued to outer cover 18 to form a semi-waterproof barrier from the external environment. In this particular figure, heating element 22 and heating coil 24 are also shown. Heating element 22 encircles pocket 10 within insulation 20 or adjacent to insulation 20. Heating coil 24 winds back and forth in a snake-like pattern just beneath, or within, insulation 20, with each row between ½ inch and ¾ inch in distance from each other. This dual pattern of heating sources provided the most comprehensive capability for pocket 10 with the greatest results. In the preferred embodiment, heating element 22 and heating coil 24 may each comprise a 50 Watt and a 120 Volt electrical wire.

Figure 4:
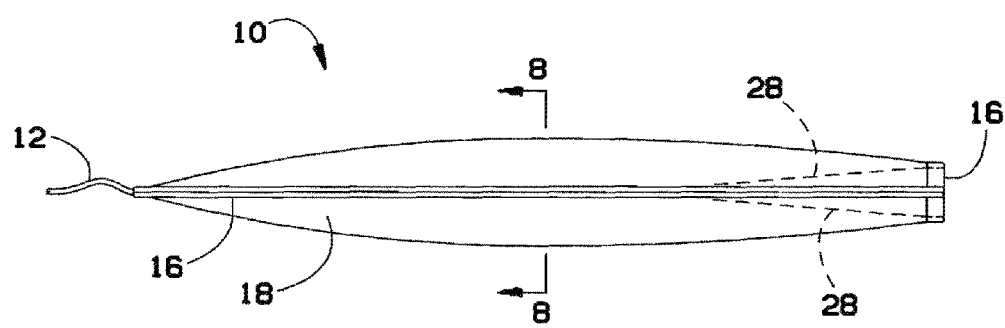
FIG. 4 illustrates a front elevation view of the preferred embodiment of the present invention.

Now referring to FIG. 4, a front elevation view of the preferred embodiment of the present invention is shown along line 8. In this closed configuration, edge trim 16 doubles up upon itself. Near the entry area on the right, baby-dry material 28 is cut in a V-pattern. This allows pocket 10 to repel any perspiration that has formed on an affected anatomical area. Baby-dry material 28 is comprised of a waterproof yet soft material that is sometimes found covering baby crib mattresses. Similar to insulation 20, baby-dry material 28 also further comprises several layers such as an inner cotton layer and an outer polyester layer in a ratio of 35% inner layer and 65% outer layer. The inner layer may be cut and attached to headliner material 26 (described infra). The external layer may be glued to edge trim 16 in order to keep it in place. In an alternate embodiment of the device, all inner layers may be inflatable in order to apply additional pressure and outer cover 18 may be stretchy or expandable.

Figure 5:
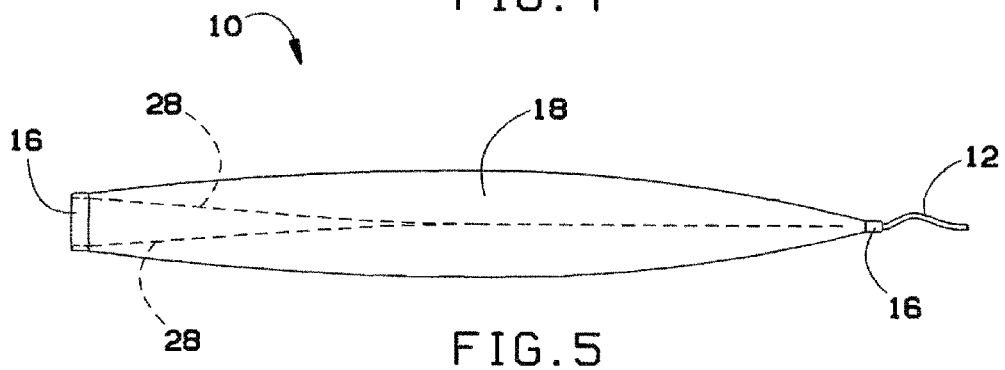
FIG. 5 illustrates a rear elevation view of the preferred embodiment of the present invention.

Now referring to FIG. 5, a rear elevation view of the preferred embodiment of the present invention is shown. In contrast to the previous diagram, the horizontal midline of pocket 10 is merely a fold, instead of a seam where edge trim 16 meets itself. Baby-dry material is now on the left in its same V-pattern, with the mouth of the V at the entry area of pocket 10. Outer cover 18 also forms an opening at the entry area.

Figure 6:
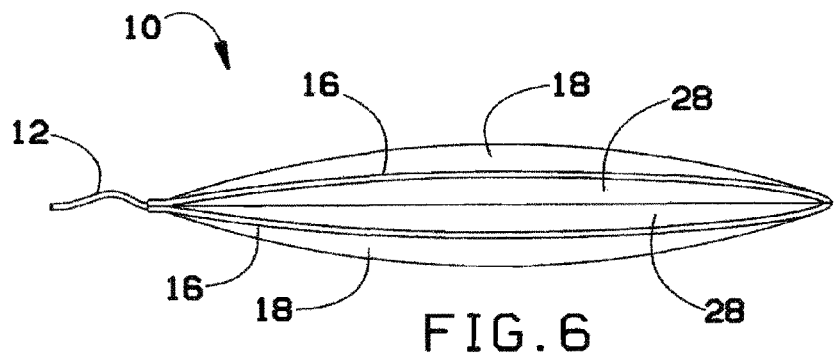
FIG. 6 illustrates a right side elevation view of the preferred embodiment of the present invention.

Now referring to FIG. 6, a right side elevation view of the preferred embodiment of the present invention is shown. This view best illustrates the entry area of pocket 10 with edge trim 16 forming a gap. In the preferred embodiment, the gap is 1-3 inches wide, but could be envisioned to be up to a few feet wide in larger versions of the invention.

Figure 7:
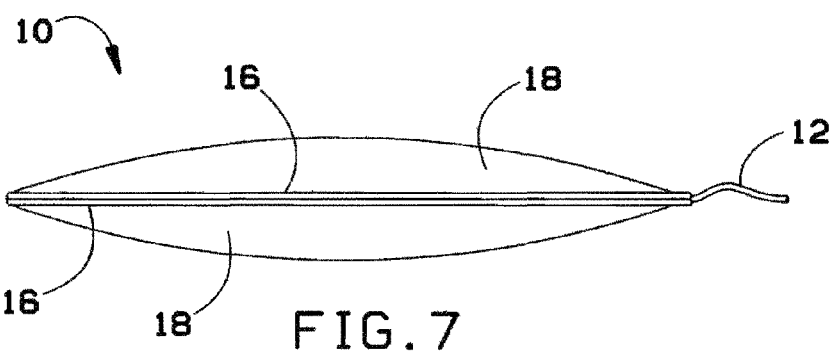
FIG. 7 illustrates a left side elevation view of the preferred embodiment of the present invention.

Now referring to FIG. 7, a left side elevation view of the preferred embodiment of the present invention is shown. Edge trim 16 and outer cover 18 are now sealed together. Power cord 12 may be extending from the front or side of pocket 10. In alternate embodiments of the present invention, power cord 12 may be reduced in size possibly leading to a small self contained battery pack.

Figure 8:
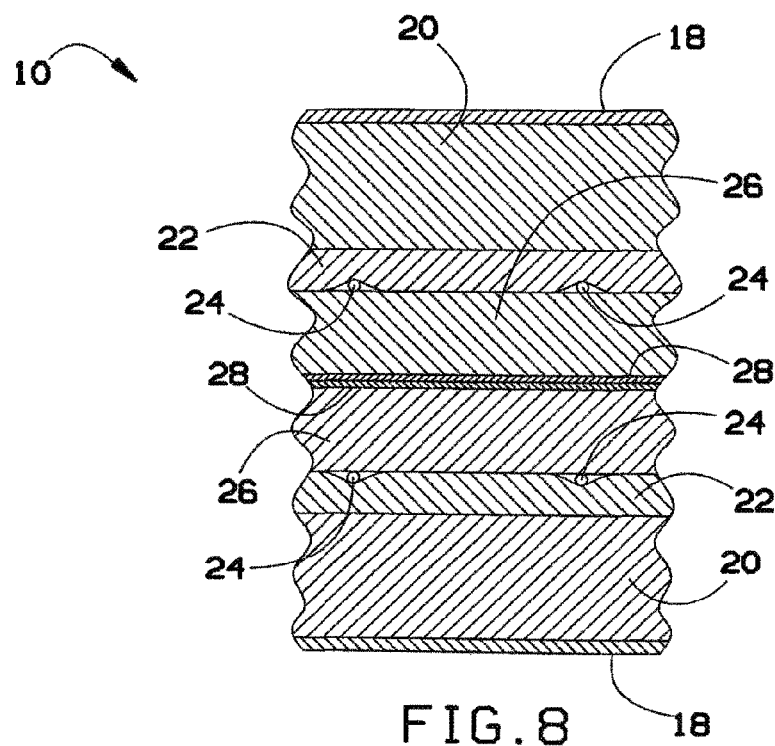
FIG. 8 illustrates a cross section of the different layers of the preferred embodiment of the present invention.

Now referring to FIG. 8, a cross section of the different layers involved in the preferred embodiment of the present invention is shown. This figure illustrates the crucial layered elements that are necessary for the utility of the invention. At the outermost border is outer cover 18. Next, when moving inward is insulation 20 and heating element 22. These two elements may be separate and adjacent to each other or intertwined together. Heating coil 24 is found inside layer insulation 20 and can possibly be attached by spray glue or other means known in the mechanical arts to the next layer, headliner material 26. In the preferred embodiment, headliner material 26 is a foam backing approximately ³⁄₁₆ to ¼ inch in width with a nylon coating or covering. This provides some structural support for pocket 10. Still moving inward further, headliner material 26 is followed by a thinner layer of baby-dry material 28.

In operation, a user may first set a desired heat level through controller 14. Next, the user may place an affected area of the body within pocket 10, or adjacent to the device when in an open configuration. After approximately fifteen minutes, the therapeutically radiated and conducted heat will warm the blood and allow the joints to move more freely while reducing pain. After approximately thirty minutes, the user may remove pocket 10 and enjoy a new level of comfort.

The present invention includes any novel feature or combination of features disclosed herein either explicitly or any generalization thereof. While the invention has been described with respect to specific examples including presently preferred modes of carrying out the invention, those skilled in the art will appreciate that there are numerous variations and permutations of the above described apparatus. Thus, the spirit and scope of the invention should be construed broadly as set forth in the previous specification or appended claims.

What is claimed is:

1. A therapeutic pocket device for alleviating the pain and symptoms of arthritis and related injuries comprising:
    a waterproof outer covering folded over on itself and sealed on at least three sides by an edge trim, thereby forming said pocket;
    an insulation material positioned within the pocket;
    a heating element positioned within the pocket adjacent to the insulation material, said heating element encircling a perimeter of the pocket;
    a heating coil positioned within the pocket adjacent to the heating element, said heating coil forming a winding pattern across the pocket;
    a headliner material positioned within the pocket adjacent to the heating element and heating coil;
    a baby-dry material positioned within the pocket adjacent to the headliner material and forming an inner surface of said pocket; and
    a power cord extending from the pocket to a power controller.

2. The device of claim 1, further comprising a battery pack electronically coupled to the power controller.

3. The device of claim 1, wherein said outer cover is composed of 65 % polyester and 35 % cotton.

4. The device of claim 1, wherein said outer cover is lined by a completely waterproof material.

5. The device of claim 1, wherein said insulation material is further comprised of four distinct layers, with the outermost layer being comprised of aluminum.

6. The device of claim 1, wherein said insulation material is comprised of at least three materials of the group consisting of wool, polyester, cotton and aluminum.

7. The device of claim 1, wherein said heating coil is spaced apart by at least half an inch.

8. The device of claim 1, wherein said heating element and said heating coil each produce a power of 50 Watts.

9. The device of claim 1, wherein said headliner material is composed of foam nylon.

10. The device of claim 1, wherein said headliner material is at least half an inch in width.

11. The device of claim 1, wherein said baby-dry material is further comprised of at least two distinct layers.

12. The device of claim 1, wherein said baby-dry material is composed of 35% cotton and 65% nylon.

13. The device of claim 1, wherein said power controller has four individual temperature settings.

14. The device of claim 1, wherein said power controller has a continuum of temperature settings.

15. A therapeutic heated pocket comprising:
- an outer covering folded over on itself and sealed on at least three sides, thereby forming said pocket;
- an insulation material positioned within the pocket;
- a heating element positioned within the pocket, said heating element encircling a perimeter of the pocket;
- a heating coil positioned within the pocket, said heating coil forming a winding pattern across the pocket;
- a headliner material positioned within the pocket;
- a baby-dry material positioned within the pocket; and
- a power controller interconnected with and configured for adjusting the heat emitted by the heating element and heating coil.

* * * * *